US008641600B2

(12) United States Patent
Nelson

(10) Patent No.: US 8,641,600 B2
(45) Date of Patent: Feb. 4, 2014

(54) STIMULATION AID DEVICE

(75) Inventor: Sammy Nelson, Stevenson Ranch, CA (US)

(73) Assignee: Evolved Novelties, Inc., Chatsworth, CA (US)

( * ) Notice: Subject to any disclaimer, the term of this patent is extended or adjusted under 35 U.S.C. 154(b) by 186 days.

(21) Appl. No.: 13/362,882

(22) Filed: Jan. 31, 2012

(65) Prior Publication Data

US 2013/0197301 A1 Aug. 1, 2013

(51) Int. Cl.
*A61F 5/00* (2006.01)
(52) U.S. Cl.
USPC .............................................. 600/38; 601/46
(58) Field of Classification Search
USPC .......................... 600/38–41; 601/46; 128/844
See application file for complete search history.

(56) References Cited

U.S. PATENT DOCUMENTS

| | | | |
|---|---|---|---|
| 3,623,481 A | 11/1971 | Curran | |
| 4,203,432 A | 5/1980 | Koch | |
| 4,834,115 A | 5/1989 | Stewart | |
| 5,397,294 A | 3/1995 | Hwang | |
| 5,524,638 A | 6/1996 | Lyons | |
| 6,390,095 B1 | 5/2002 | Magnusson | |
| D459,469 S | 6/2002 | Johnson | |
| D460,172 S | 7/2002 | Johnson | |
| 6,485,408 B2 | 11/2002 | Orten | |
| 6,547,718 B1 | 4/2003 | Yasue | |
| 6,659,938 B1 | 12/2003 | Orlowski et al. | |
| 6,705,987 B2 | 3/2004 | Anderson et al. | |
| D496,458 S | 9/2004 | Lin | |
| 6,790,189 B2 | 9/2004 | Kobayashi et al. | |
| 6,863,649 B2 | 3/2005 | Yasue | |
| 6,907,883 B2 | 6/2005 | Lin | |
| D523,958 S | 6/2006 | Fang | |
| 7,108,668 B2 | 9/2006 | Fang | |
| D552,748 S | 10/2007 | Gromosaik et al. | |
| D552,749 S | 10/2007 | Gromosaik et al. | |
| D552,750 S | 10/2007 | Gromosaik et al. | |
| D566,289 S | 4/2008 | Tasker et al. | |
| D567,957 S | 4/2008 | Critchley | |
| D581,544 S | 11/2008 | Adams | |
| D637,302 S | 5/2011 | Post | |
| 2002/0103415 A1 | 8/2002 | Manska et al. | |
| 2002/0188235 A1 | 12/2002 | Manska | |
| 2005/0155609 A1 | 7/2005 | Lin | |
| 2005/0283044 A1 | 12/2005 | Chang | |
| 2006/0178602 A1 | 8/2006 | Teng et al. | |

*Primary Examiner* — John Lacyk
(74) *Attorney, Agent, or Firm* — David J. Pitman; Fulwider Patton LLP

(57) ABSTRACT

A sex stimulation aid comprises a circular ring defining a first opening sized to fit over the root of a male penis, the ring having an outside diameter, the first opening having an inside diameter and a first elongate axis. A second opening has a second inside diameter and a second elongate axis, the second axis and the first axis extending parallel to each other and offset by a first distance. A third opening has a third inside diameter and a third elongate axis, the third axis and the first axis extending in directions perpendicular to each other and offset by a second distance. A first vibration element and a second vibration element are included.

8 Claims, 2 Drawing Sheets

STIMULATION AID DEVICE

BACKGROUND

The present invention relates to a penile erection support ring configured to assists a male person in achieving and maintaining an erection when mounted on a penis of the male during sexual intercourse.

Problems that occur during sexual intercourse arise from a decline in the ability to achieve or maintain an erection, and are well known. Such problems result in unsuccessful sexual intercourse with a partner which may be highly distressing for both partners involved. A diversity of devices and medications to remedy or ameliorate this problem have been developed.

A decline in the ability to achieve an erection, or the achievement of an unsatisfied erection, typically results from a variety of causes. The problem may present itself as a number of different symptoms. If the penis of an individual is unable to erect because of his mental or physical disorder, a vacuum device or a medicine may be used to force the penis to erect. The decline in ability to achieve an erection may result from not only mental or physical disorder, but may also decline as a result of failing physical fitness with age, stress accumulated with fatigue, or unresponsiveness to repeating of monotonous sexual acts. However, a majority of males who experience a weak erection typically find that the cause may be found somewhere in the conduct of their daily lives. Such males do not attempt to use a large-scale device such as a vacuum device at each sexual intercourse, and also typically avoid using a drug which could have an undesirable side effect. Due to embarrassment, such males may not discuss these problems with their female partner or with their doctor.

In an attempt to resolve these problems, small scale penis rings have been developed that a male my wear without embarrassment. However, while such rings as are known in the art may assure sexual sensation to only one of the partners during use, insufficient consideration is given to the needs of both partners.

Thus, there is a need for a male physical aid that is easily accepted by a partner, is simple in structure, is easy to use, and which provides stimulation to both the male and the female partner.

SUMMARY OF THE INVENTION

In a preferred embodiment, the sex stimulation aid of the present embodiment comprises a substantially circular shaped ring defining a first centrally positioned cylindrical opening sized to fit over the root of a male penis, the ring having an outside diameter, the first cylindrical opening having a first inside diameter and a first elongate axis. The ring further defines a second cylindrical opening having a second inside diameter and a second elongate axis, the second axis and the first axis extending in directions parallel to each other and offset from each other by a first distance. Further, the ring defines a third cylindrical opening having a third inside diameter and a third elongate axis, the third axis and the first axis extending in directions perpendicular to each other and offset from each other by a second distance. A first vibration element having a fourth diameter is provided, and is positioned within the second opening. A second vibration element having a fifth diameter is provided, positioned within the third opening. In a preferred aspect, the stimulation aid is formed from foam rubber, and the second diameter is smaller than the fourth diameter, before the first vibration element is inserted into the second opening. In another preferred aspect, the third diameter is smaller than the fifth diameter before the second vibration element is inserted into the third opening. Thus, the vibration elements are sized to stretch the openings in the ring into which they are inserted. In yet further preferred aspects, the first offset distance is between one inch and two inches, and the second offset distance is also between one inch and two inches.

In other preferred aspects of the stimulation aid, the ring includes ribs that extend radially along the surface of the ring, each rib standing above the surface of the ring by between an eighth of an inch and one third of an inch. Yet a further preferred aspect, the ring is configured so that the second vibration element, while positioned within the third opening, is simultaneously positioned partially within the first opening so that a penis inserted into the first opening will be in direct contact with the second vibration element.

These, and other advantages of the invention will become apparent when read in conjunction with the description of the drawings, the drawings, and the detailed description of the preferred embodiments.

DETAILED DESCRIPTION OF THE PREFERRED EMBODIMENTS

Figure 1:
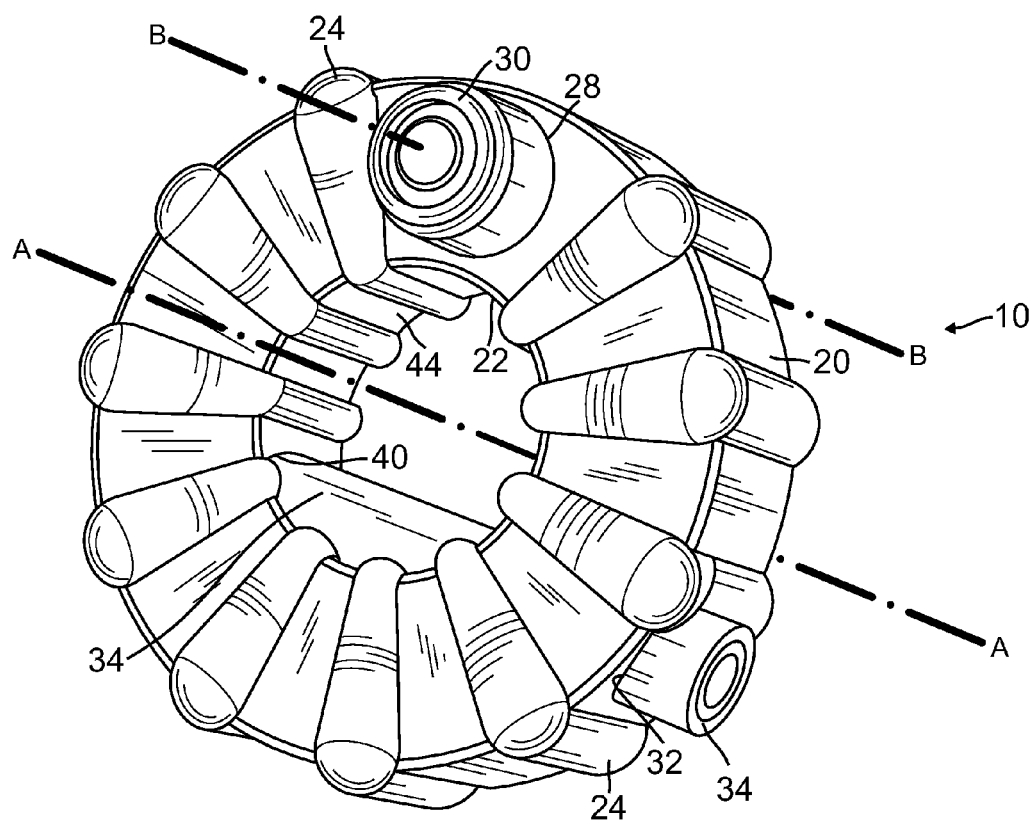
FIG. 1 is a perspective view of a stimulation aid having features of the present invention.

With reference to the figures, a preferred embodiment of the stimulation aid device 10 of the present invention is described. In a first aspect, the invention includes a substantially circular annulus or ring 20 that defines a first central opening 22 that surrounds a central axis A-A of the ring. The ring is preferably formed of foam rubber, or a similar substance, having a texture that is suitably flexible for the purpose of being mounted on the root of a male penis.

The ring may be commercially manufactured in different sizes. To satisfy its intended purpose, it preferably has a circular outside diameter of between about three to four inches, and the first opening 22 has a substantially circular inside diameter of between about one to three inches. The thickness of the ring is preferably between one quarter and three quarters of an inch.

The ring may include ribs 24 positioned to extend radially from a center point lying on central axis A-A. The ribs may take the form of radial protrusions that extend from the otherwise planar surface of the ring, the extent of each protrusion being about an eighth to a third of an inch, and being spaced between about thirty to forty degrees apart around the central axis, so that there may be between about ten to twenty radial protrusions on the ring.

In one important aspect, the ring includes a second opening 28 with a central axis B-B, positioned in between the inside diameter and the outside diameter of the ring. The two axes of the first 22 and second 28 openings, A-A and B-B respectively, are parallel to each other and are offset from each other by a preferred distance "d1" (FIGS. 2 and 3) of between one and two inches. The second opening is configured to receive a first, known, cylindrically shaped vibration element 30 that includes its own battery for power supply. (FIG. 1) When switched on, the vibration element will, by known means, impart a vibration to the entire ring 20. Preferably, the second opening 28 has a diameter that is sized to be slightly smaller than the diameter of the vibration element 30 before the vibration element is inserted into the opening 28, so that the flexible elasticity and the surface texture of the material from which the ring 20 is formed is sufficient to grasp and hold the vibration element, and to resist any sliding action between the ring 20 and the first vibration element 30.

Figures 2, 3:
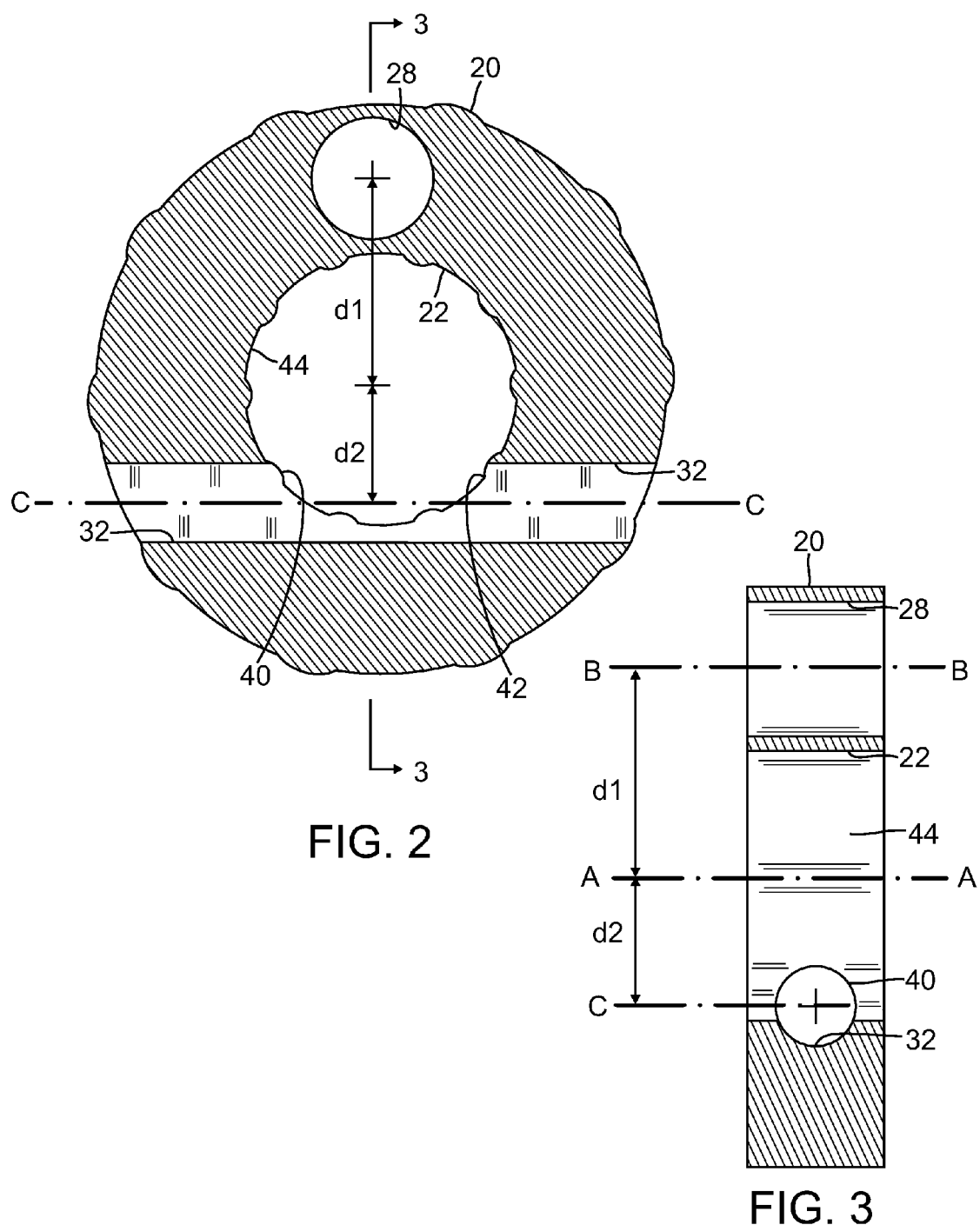
FIG. 2 is a front sectional view of a component of the stimulation aid of FIG. 1.
FIG. 3 a left sectional view of a component of the stimulation aid shown in FIG. 1.

In another important aspect, the ring 20 includes a third opening 32 with a central axis C-C. The third opening is positioned to extend so that the axis C-C is perpendicular to the axis A-A, and is offset from the center of the ring by a distance "d2" (FIGS. 2 and 3). The distance "d2," and the radius of the third opening are chosen so that the third opening preferably causes lateral openings 40, 42 to be formed in the internal cylindrical wall 44 of the central first opening 22. In a preferred embodiment, "d2" is between one and two inches. The third opening is configured to receive a second, known, cylindrically shaped vibration element 34 that includes its own battery for power supply. When switched on, the vibration element 34 will, by known means, impart a vibration to the entire ring 20. Preferably, the third opening 28 is sized to have a diameter that is slightly smaller than the diameter of the vibration element 34 before the vibration element is inserted into the opening 32, so that the flexible elasticity and the surface texture of the material from which the ring 20 is formed is sufficient to grasp and hold the vibration element, and to resist any sliding action between the ring 20 and the second vibration element 34. Because of the lateral openings 40, 42 formed in the internal cylindrical wall 44 of the first opening 22, the second vibration element 34 may partially extend into the space defined by the first opening 22, as seen in FIG. 1. This aspect has a desired advantageous effect, described more fully below.

Thus, in its final configuration, the present invention is configured to include two cylindrical vibration elements 30, 34, positioned with longitudinal axes perpendicular to each other and set apart from each other so that the first vibration element is located on one side of the central opening 22, and the second vibration element 34 is located diametrically opposite the first vibration element 30, with the central first opening 22 situated between the two vibration elements, as exemplified in FIG. 1.

In use, the stimulation device may be used as follows. The user first inserts the first vibration element 30 into the second opening 28, and the second vibration element 34 into the third opening 32 as seen in FIG. 1. In each case, the vibration element will stretch the diameter of the second 28 and third 32 openings slightly upon insertion therein, to cause the vibration elements to be securely received. Thereafter, the user may insert the ring over the root of the male penis, and may orient the ring so that first vibration element 30, extending parallel with the penis and axis A-A, is on the upper portion of the ring, and the second vibration element 34, extending transverse to the penis, is on the lower portion of the ring. If not already switched on, the two vibration elements may be switched on, typically by pressing an end of each of the vibration elements. In a preferred aspect as described above, the second vibrator 34, by extending through the third cylindrical opening 32, will also extend partially into the space defined by the first opening 22, as seen in FIG. 1. As a consequence, as it will be appreciated, the second vibration element will come into direct contact with the male penis which is inserted into the first opening 22. This has the advantageous effect of providing a more direct and un-attenuated vibration sensation to the male partner.

Under this novel configuration, the stimulation aid is equipped with two vibration elements, namely a first element positioned and oriented to provide contact with the sex organ of the female partner, from in front, and a second element positioned and oriented to provide direct contact with the sex organ of the male partner. Advantageously, both vibration elements may be switched on simultaneously, or, only the male oriented element, or only the female oriented element may be switched on alone, depending on the needs of the partners.

Thus, there is described an advantageous and novel sex stimulation aid that provides a solution to problems encountered in the prior art. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

I claim:

1. A sex stimulation aid comprising:
a substantially circular shaped ring defining a first centrally positioned cylindrical opening sized to fit over the root of a male penis, the ring having an outside diameter, the first cylindrical opening having a first inside diameter and a first elongate axis,
wherein the ring further defines a second cylindrical opening having a second inside diameter and a second elongate axis, the second axis and the first axis extending in directions parallel to each other and offset from each other by a first distance,
and further, wherein the ring defines a third cylindrical opening having a third inside diameter and a third elongate axis, the third axis and the first axis extending in directions perpendicular to each other and offset from each other by a second distance;
a first vibration element having a fourth diameter positioned within the second opening; and
a second vibration element having a fifth diameter positioned within the third opening.

2. The stimulation aid of claim 1, wherein the ring is formed from foam rubber.

3. The stimulation aid of claim 1, wherein the second diameter is smaller than the fourth diameter, before the first vibration element is inserted into the second opening.

4. The stimulation aid of claim 1, wherein the third diameter is smaller than the fifth diameter before the second vibration element is inserted into the third opening.

5. The stimulation aid of claim 1, wherein the first offset distance is between one inch and two inches.

6. The stimulation aid of claim 1, wherein the second offset distance is between one inch and two inches.

7. The stimulation aid of claim 1, wherein the ring includes ribs that extend radially along the surface of the ring, each rib standing above the surface of the ring by between an eighth of an inch and one third of an inch.

8. The stimulation aid of claim 1, wherein the ring is configured so that the second vibration element, while positioned within the third opening, is simultaneously positioned partially within the first opening.

* * * * *